(12) United States Patent
Majeed et al.

(10) Patent No.: US 9,365,486 B2
(45) Date of Patent: Jun. 14, 2016

(54) SYNTHESIS OF CALEBIN-A AND ITS BIOLOGICALLY ACTIVE ANALOGS

(71) Applicants: Muhammed Majeed, Edison, NJ (US); Kalyanam Nagabhushanam, East Windsor, NJ (US); Anju Majeed, Piscataway, NJ (US); Samuel Manoharan Thomas, Bangalore (IN)

(72) Inventors: Muhammed Majeed, Edison, NJ (US); Kalyanam Nagabhushanam, East Windsor, NJ (US); Anju Majeed, Piscataway, NJ (US); Samuel Manoharan Thomas, Bangalore (IN)

( * ) Notice: Subject to any disclaimer, the term of this patent is extended or adjusted under 35 U.S.C. 154(b) by 0 days.

(21) Appl. No.: 14/320,649

(22) Filed: Jul. 1, 2014

(65) Prior Publication Data

US 2016/0002141 A1  Jan. 7, 2016

(51) Int. Cl.
*C07C 67/10* (2006.01)
*C07C 67/11* (2006.01)

(52) U.S. Cl.
CPC .................. *C07C 67/10* (2013.01); *C07C 67/11* (2013.01)

(58) Field of Classification Search
None
See application file for complete search history.

(56) References Cited

PUBLICATIONS

Darrick et al., Bioorganic & Medicinal Chemistry Letters 11 (2001) 2541-2543.*

* cited by examiner

*Primary Examiner* — Karl J Puttlitz

(57) ABSTRACT

Disclosed is a simple, economical, industrially scalable green synthetic process for Calebin-A and its biologically active analogs.

8 Claims, 1 Drawing Sheet

Prior Art
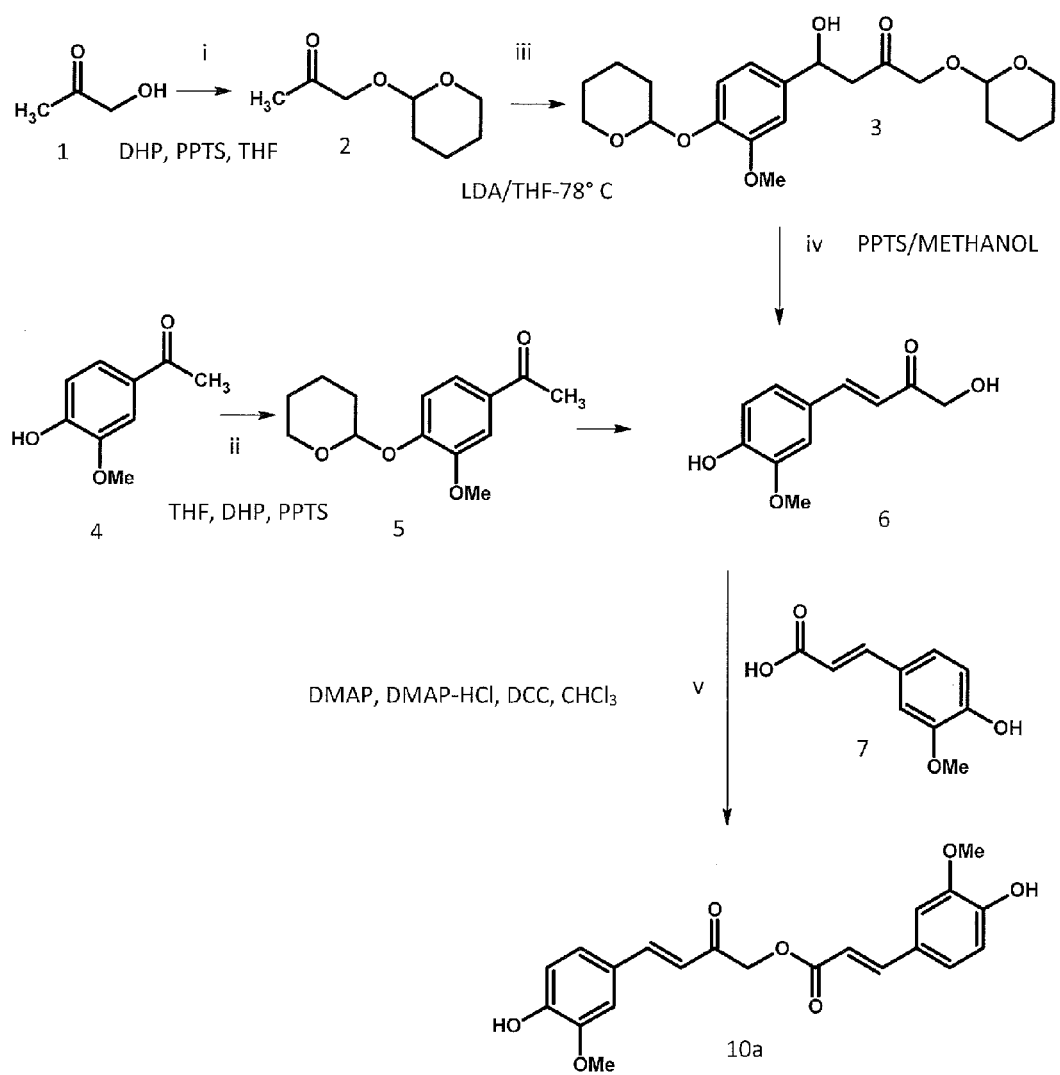

SYNTHESIS OF CALEBIN-A AND ITS BIOLOGICALLY ACTIVE ANALOGS

BACKGROUND OF THE INVENTION

1. Field of the Invention

The present invention in general relates to calebinoids. More specifically, the present invention relates to a simple, economical and scalable green process for the synthesis of Calebin A and its biologically active analogs.

2. Description of Prior Art

Darrick S. H. L. Kim and So-Young Park isolated and identified Calebin-A from *Curcuma longa* in 2001 (Park S. Y. & Kim, D. S. H. L., J. Nat. Prod., 2002, 65, 1227-1231). Demethoxycalebin-Al and demethoxycalebin-A2 have been isolated as a pair from *Curcuma longa* by Feng Qiu et al. in 2007 (Zeng, Y. C., Qiu, F., Takahashi, K., Liang, J. M., Qu, G. X. & Yao, X. S., Chem. Pharm. Bull., 2007, 55, 940-943). By analogy, bisdemethoxycalebin-A may also be present in *Curcuma longa* though not reported yet. Darrick S. H. L. Kim and Jin Y. Kim synthesized Calebin-A and some of its analogs through a circuitous route (five steps) starting from 1-hydroxyacetone (1) (Kim, D. S. H. L. & Kim, J. Y., Bioorg. Med. Chem. Lett., 2001, 11, 2541-2543). The calebinoids having free p-hydroxy group are biologically active. Subsequently D. H. S. L. Kim has patented the pharmaceutical compositions of Calebin-A and its analogs as useful for prevention and treatment of β-amyloid peptide-induced disease [U.S. Pat. No. 7,572,829 B2 (2009). This synthesis has been represented as FIGURE-Prior Art. In short, this prior art synthetic scheme involves protection of 1-hydroxyacetone (1) and vanillin (4) as their tetrahydropyranyl (THP) ethers (2 & 5) using dihydropyran. THP ether of 1-hydroxyacetone (2) is treated with Lithium diisopropylamide (LDA) at low temperature (−78° C.) to generate the lithio anion at the α-methyl of the keto group. This lithio anion adds to the aldehyde group of the THP ether of vanillin (5) to give the β-hydroxy-ketone (3). This is dehydrated and deprotected to Feruloylmethanol (6) which is coupled to ferulic acid (7) in the presence of 4-dimethylaminopyridine (DMAP), DMAP-HCl and N,N-Dicyclohexylcarbodiimide (DCC) to get Calebin-A (10a). The synthetic scheme for Calebin-A discussed herein above is the only known for Calebin-A and its analogs. However, it suffers from the following technical disadvantages.

1. The starting material 1-hydroxyacetone is expensive.
2. The condensation of vanillin with 1-hydroxyacetone involves protection of the hydroxyls as their THP ethers to avoid Lithium diisopropylamide reacting with hydroxyls.
3. 4-dimethylaminopyridine and N, N-Dicyclohexyl carbodiimide are also expensive.
4. The synthesis involves a minimum of five steps, very low temperature (−78° C.), pyrophoric and moisture sensitive reagents.

All aforesaid factors make this process industrially non-feasible for scale up.

It is therefore the principle objective of the present invention to describe a simple, economical, scalable green process for the synthesis of Calebin-A and its analogs.

The present invention fulfills the principle objective and provides further related advantages.

SUMMARY OF THE INVENTION

The present invention discloses a simple, economical, green and industrially scalable synthetic process for Calebin-A and its biologically active analogs. The disclosed invention has the following advantages. They are, 1. It is a single step synthetic scheme;
2. Economic viability is achieved in terms of low costs of the synthetic process;
3. It is an example of green process that is environmental friendly; and
4. The synthetic scheme assures industrial scalability.

BRIEF DESCRIPTION OF THE DRAWINGS

FIGURE-Prior Art shows the prior art synthetic scheme for Calebin A

DESCRIPTION OF THE MOST PREFERRED EMBODIMENT

In the most preferred embodiment, the present invention relates to a general synthetic process for the compound represented by general STR#3 wherein the dotted configuration . . . is double bond; R1=R3=—OH; R2/R4 is selected from the group consisting of H, OMe, ORa and X wherein Ra is alkyl, alkenyl, or alkynyl and X is F, Cl, Br, or I, said syntheltic process comprising the steps of A. Mixing solvent dissolved iodomethyl ketone of general structure STR#1 having substituents R1 and R2 as defined vide supra with aqueous solution of the sodium or potassium salt of acid of general structure (STR#2) [1.0-4.0] mole equivalent, where M=Na+ or K+ and R3 and R4 as defined vide supra;

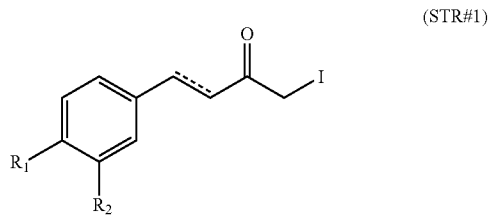
(STR#1)

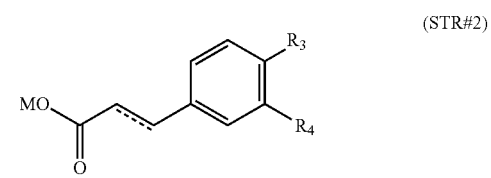
(STR#2)

B. Stirring the mixture of Step A at ambient temperature (5° C.-30° C.) in the presence of a phase transfer catalyst (5-10 mole percent with respect to the iodide) and stirring the mixture for 24-72 hours;

C. Separating the organic layer from the product of Step B, washing with aqueous sodium hydrogen carbonate solution followed by drying over anhydrous sodium sulfate, filtering and stripping off the solvent under vacuum followed by crystallization of the crude from ethyl acetate or ethanol to get compound represented by general structure STR#3 as pale yellow crystalline solid in 50%-60% yield.

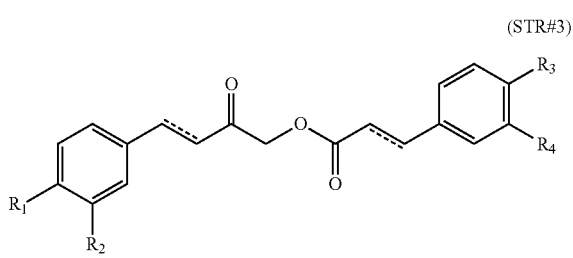

In another most preferred embodiment, the present invention relates to a simple, economical, industrially scalable green synthetic scheme for Calebin-A and its demethoxy analogs as represented herein below.

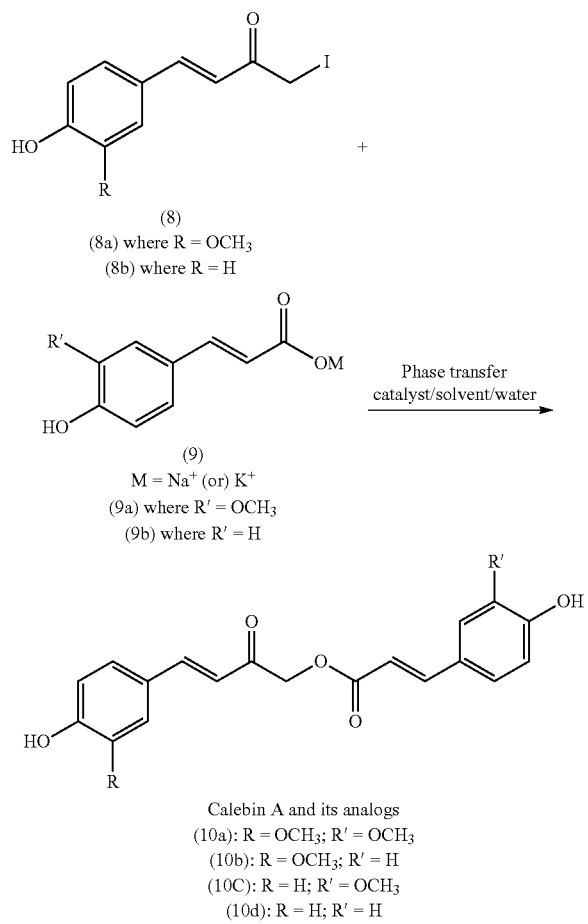

Specifically, the present invention relates to a general synthetic process for Calebin-A (Feruloylmethyl ferulate-10a) and its demethoxy analogs (Feruloylmethyl 4-hydroxycinnamate-10b, 4-Hydroxycinnamoylmethyl ferulate-10c and 4-Hydroxycinnamoylmethyl 4-hydroxycinnamate-10d), said process comprising the steps of:

A. Mixing feruloyl or 4-hydroxycinnamoyliodomethane (8a or 8b, 0.015 mol) dissolved in a solvent with the aqueous solution of sodium or potassium salt of ferulic acid or 4-hydroxycinnamic acid ((9a or 9b), 1.0-4.0 mole equivalent);

B. Stirring the mixture of Step A at ambient temperature (5° C.-30° C.) in the presence of a phase transfer catalyst (5-10 mole percent with respect to the iodide) and stirring the mixture for 24-72 hours;

C. Separating the organic layer from the product of Step B, washing with aqueous sodium hydrogen carbonate solution followed by drying over anhydrous sodium sulfate, filtering and stripping off the solvent under vacuum followed by crystallization of the crude from ethyl acetate or ethanol to get Calebin-A (Feruloylmethyl ferulate-10a) or its demethoxy analogs (Feruloylmethyl 4-hydroxycinnamate-10b, 4-Hydroxycinnamoylmethyl ferulate-10c and 4-Hydroxycinnamoylmethyl 4-hydroxycinnamate-10d) as pale yellow crystalline solids in 50-60% yield.

In specific embodiments, the ideal solvent for dissolving Feruloyl or 4-hydroxycinnamoyliodomethane as mentioned herein above is one selected from group comprising dichloromethane, chloroform, ethyl acetate and tetrahydrofuran among others.

In further specific embodiments, ideal phase transfer catalysts used in aforementioned synthetic scheme is one selected from group comprising tetrabutylammonium bromide, tetrabutylammonium hydrogensulfate, benzyltributyl ammonium chloride, benzyltriethylammonium chloride and benzyltrimethyl ammonium chloride among others.

Specific examples of the general synthetic scheme for Calebin A and its demethoxy analogs discussed herein above are provided in the following paragraphs. Feruloyliodomethane and 4-Hydroxycinnamoyliodomethane used in examples included herein below were prepared according to a reported method (Wang, Z., Yin, G., Qin, J., Gao, M., Cao, L & Wu, A., Synthesis, 2008, 22, 3675-3681).

EXAMPLE 1

Calebin-A (Feruloylmethyl Ferulate, 10a)

Calebin-A (10a) was prepared by reacting feruloyliodomethane with sodium or potassium salt of ferulic acid with reaction steps and conditions maintained as mentioned in the general synthetic scheme discussed herein above in Para 0010. The yield of the product was 60%.

Calebin-A (Feruloylmethyl ferulate, 10a): Pale yellow solid; m.p. 138-140° C.; $^1$H NMR (Acetone-d6, 300 MHz): δ 3.902 (s, 3H), 3.929 (s, 3H), 5.106 (s, 2H), 6.518 (d, J=15.9 Hz, 1H), 6.856 (d, J=16.2 Hz, 1H), 6.886 (d, J=8.4 Hz, 1H), 6.892 (d, J=8.4 Hz, 1H), 7.180 (dd, J=8.4 Hz, 1.8 Hz, 1H), 7.214 (dd, J=8.4 Hz, 1.8 Hz, 1H), 7.375 (d, J=1.8 Hz, 1H), 7.386 (d, J=1.8 Hz, 1H), 7.666 (d, J=16.2 Hz, 1H), 7.671 (d, J=15.9 Hz, 1H), 8.246 (s, 1H), 8.309 (s, 1H).

$^{13}$C NMR (Acetone-d6, 75 MHz): δ 56.267, 56.296, 67.927, 111.290. 111.524, 116.077, 116.201, 120.322, 124.165, 124.494, 127.349, 127.408, 144.389, 146.505, 148.752, 150.209, 150.501, 166.898, 192.963.

LC-MS (+APCI): m/z 385 (M$^+$+1); LC-MS (−APCI): m/z 383 (M$^+$−1).

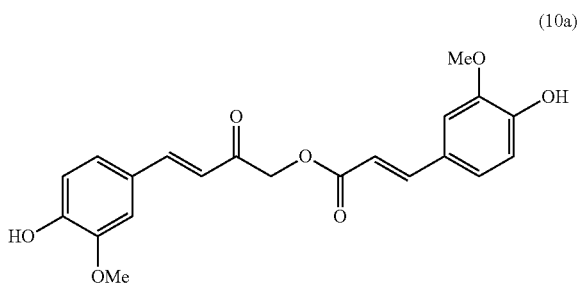 [SMILES: COc1cc(/C=C/C(=O)COC(=O)/C=C/c2ccc(O)c(OC)c2)ccc1O]

(10a)

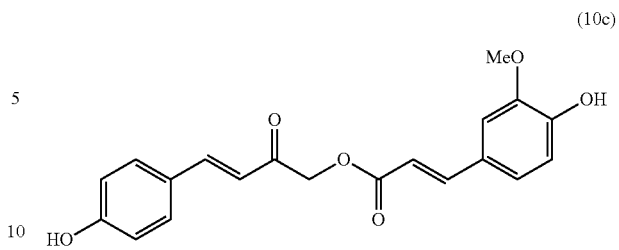

(10c)

EXAMPLE 2

Demethoxycalebin-A1 (Feruloylmethyl 4-Hydroxycinnamate 10b)

Demethoxycalebin-A1 (Feruloylmethyl 4-hydroxycinnamate 10b) was prepared by reacting feruloyliodomethane with sodium or potassium salt of 4-hydroxycinnamic acid with reaction steps and conditions maintained as mentioned in the general synthetic scheme discussed herein above in Para 0010. The yield of the product was 50%.

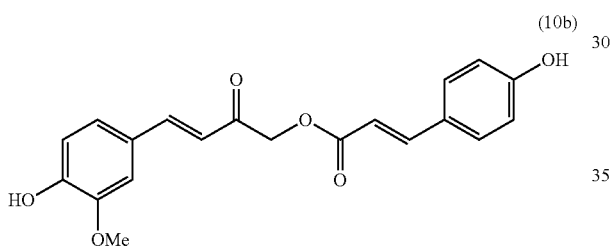

(10b)

Demethoxycalebin-A1 (Feruloylmethyl 4-hydroxycinnamate, 10b): Pale yellow solid; m.p. 181.4-183.4° C.;

$^1$H NMR (DMSO-d6, 300 MHz): δ 3.815 (s, 3H), 5.132 (s, 2H), 6.508 (d, J=16.2 Hz, 1H), 6.813 (d, J=8.4 Hz, 2H), 6.825 (d, J=8.4 Hz, 1H), 6.842 (d, J=16.8 Hz, 1H), 7.173 (dd, J=8.4 Hz, 1.5 Hz, 1H), 7.336 (d, J=1.5 Hz, 1H), 7.592 (d, J=8.4 Hz, 2H), 7.623 (d, J=16.8 Hz, 1H), 7.626 (d, J=16.2 Hz, 1H), 9.814 (s, 1H), 10.135 (s, 1H).

$^{13}$C NMR (DMSO-d6, 75 MHz): δ 55.764, 55.793, 67.263, 111.431, 113.656, 115.778, 115.961, 119.541, 123.837, 125.162, 125.763, 130.637, 143.959, 145.643, 148.110, 149.925, 160.121, 166.189, 192.753.

LC-MS (+APCI): m/z 355 (M$^+$+1); LC-MS (−APCI): m/z 353 (M$^+$−1).

EXAMPLE 3

Demethoxycalebin-A2 (4-Hydroxycinnamoylmethyl Ferulate 10c)

Demethoxycalebin-A2 (4-Hydroxycinnamoylmethyl ferulate 10c) was prepared by reacting 4-hydroxycinnamoyliodomethane with sodium or potassium salt of ferulic acid with reaction steps and conditions maintained as mentioned in the general synthetic scheme discussed herein above in Para 0010. The yield of the product was 50%.

Demethoxycalebin-A2 (4-Hydroxycinnamoylmethyl ferulate, 10c): Cremish solid, m.p. 175.7-177.7° C.

$^1$H NMR (DMSO-d$_6$, 300 MHz): δ 3.819 (s, 3H), 5.127 (s, 2H), 6.591 (d, J=16.2 Hz, 1H), 6.773 (d, J=16.2 Hz, 1H), 6.807 (d, J=8.4 Hz, 1H), 6.825 (d, J=8.4 Hz, 2H), 7.157 (dd, J=8.4 Hz, 1.8 Hz, 1H), 7.357 (d, J=1.8 Hz, 1H), 7.589 (d, J=8.4 Hz, 2H), 7.614 (d, J=16.2 Hz, 1H), 7.631 (d, J=16.2 Hz, 1H), 9.731 (s, 1H), 10.207 (s, 1H).

$^{13}$C NMR (DMSO-d$_6$, 75 MHz): δ 55.786, 55.815, 67.249, 111.372, 113.934, 115.632, 116.042, 119.211, 123.450, 125.236, 125.631, 130.835, 143.601, 145.936, 148.058, 149.596, 160.370, 166.197, 192.775.

LC-MS (+APCI): m/z 355 (M$^+$+1); LC-MS (−APCI): m/z 353 (M$^+$−1).

EXAMPLE 4

Bisdemethoxycalebin-A (4-Hydroxycinnamoylmethyl 4-hydroxycinnamate, 10d)

Bis-demethoxycalebin-A (4-Hydroxycinnamoylmethyl 4-hydroxycinnamate, 10d) was prepared by reacting 4-hydroxycinnamoyliodomethane with sodium or potassium salt of 4-hydroxycinnamic acid with reaction steps and conditions maintained as mentioned in the general synthetic scheme discussed herein above in Para 0010. The yield of the product was 55%.

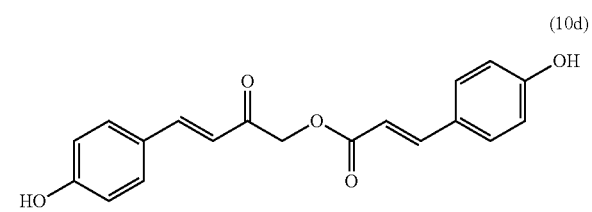 [SMILES: O=C(/C=C/c1ccc(O)cc1)COC(=O)/C=C/c1ccc(O)cc1]

(10d)

Bisdemethoxycalebin-A (4-Hydroxycinnamoylmethyl 4-hydroxycinnamate, 10d): Pale yellow solid: m.p. 289-291° C.;

$^1$H NMR (DMSO-d$_6$, 300 MHz): δ 5.120 (s, 2H), 6.507 (d, J=15.9 Hz, 1H), 6.771 (d, J=15.9 Hz, 1H), 6.813 (d, J=8.4 Hz, 2H), 6.825 (d, J=8.4 Hz, 2H), 7.587 (d, J=8.4 Hz, 4H), 7.626 (d, J=15.9 Hz, 2H), 10.140 (s, 1H), 10.201 (s, 1H).

$^{13}$C NMR (DMSO-d$_6$, 75 MHz): δ 67.293, 113.648, 115.976, 116.086, 119.219, 125.177, 125.265, 130.645, 130.879, 143.645, 145.658, 160.136, 160.407, 166.204, 192.819.

LC-MS (+APCI): m/z 325 (M$^+$+1); LC-MS (−APCI): m/z 323 (M$^+$−1).

The examples included herein substantiate the most preferred embodiment of the invention. These examples should

We claim:

1. A process for preparing a compound of formula STR#3 wherein dotted configurations - - - is a double bond; $R_1$ is selected from the group consisting of OH, OMe, $OR_a$ and X wherein $R_a$ is alkyl, alkenyl, or alkynyl and X is F, CI, Br, or I; $R_2$ is selected from group consisting of H, OMe, and $OR_2$ wherein $R_a$ is alkyl, alkenyl, or alkynyl; R3 is selected from the group consisting of OH, OMe, $OR_a$ and X where $R_a$ is alkyl, alkenyl, or alkynyl and X is F, CI, Br, or I; $R_4$ is selected from group consisting of H, OMe, and $OR_a$ where $R_a$ is alkyl, alkenyl, or alkynyl; and $R_1$ is OH, $R_2$ is OMe, $R_3$ is OH and $R_4$ is H, said process comprising the steps of A. providing a mixture iodomethyl ketone of formula STR#1, wherein $R_1$ and $R_2$ are defined above, and 1.0-4.0 mole equivalents of an aqueous solution of a sodium or potassium salt of an acid of formula STR#2, wherein M is $Na^+$ or $K^+$ and $R_3$ and $R_4$ are defined above;

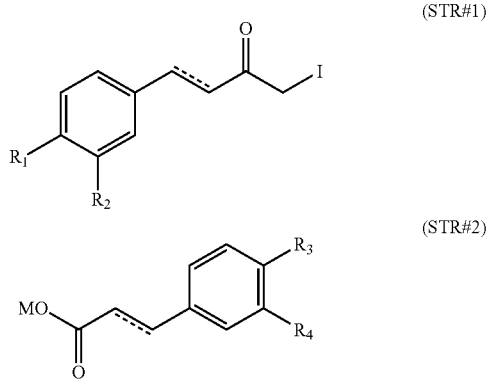

B. stirring the mixture of Step A in the presence of a phase transfer catalyst at 5° C.-30° C. for 24-72 hours, wherein said catalyst is present at 5- mole percent with respect to STR#1;

C. separating an organic layer from the product of Step B, washing said layer with an aqueous sodium hydrogen carbonate solution, drying over anhydrous sodium sulfate, filtering, stripping off solvent under vacuum and crystallizing from ethyl acetate or ethanol to provide a compound of formula STR#3 as a crystalline solid at 50%-60% yield

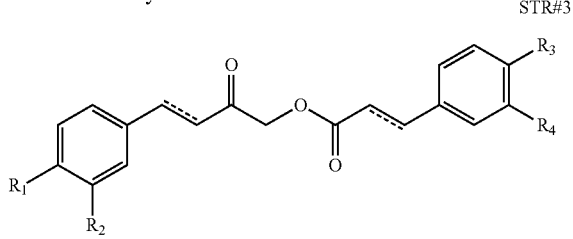

2. A process for preparing feruloylmethyl ferulate or demethoxy analogs thereof, wherein said analogs are selected from the group consisting of feruloylmethyl 4-hydroxycinnamate, 4-hydroxycinnamoylmethyl ferulate and 4-hydroxycinnamoylmethyl 4-hydroxycinnamate, said process comprising the steps of:

A. providing a mixture of 0.015 mols of feruloyliodomethane or 4-hydroxycinnamoyliodomethane dissolved in a solvent with an 1.0-4.0 mole equivalents of aqueous solution of sodium or potassium salt of ferulic acid or 4-hydroxycinnamic acid;

B. stirring the mixture of Step A in the presence of a phase transfer catalyst at 5° C.-30° C. for 24-72 hours, wherein said catalyst is present at 5-10 mole percent with respect to said iodide;

C. separating an organic layer from the product of Step B, washing said layer with an aqueous sodium hydrogen carbonate solution, drying over anhydrous sodium sulfate, filtering, stripping off solvent under vacuum and crystallizing from ethyl acetate or ethanol to provide feruloymethyl ferulate, feruloylmethyl 4-hydroxycinnamate, 4-hydroxycinnamoylmethyl ferulate and 4-hydroxycinnamoylmethyl 4-hydroxycinnamate as crystalline solids in 50-60% yield.

3. The process according to claim 2 wherein synthesis of Calebin-A (Feruloylmethyl ferulate) comprises reacting feruloyliodomethane with sodium or potassium salt of ferulic acid in step A.

4. The process according to claim 2 wherein synthesis of Feruloylmethyl 4-hydroxycinnamate comprises reacting feruloyliodomethane with sodium or potassium salt of 4-hydroxycinnamic acid in step A.

5. The process according to claim 2 wherein synthesis of 4-Hydroxycinnamoylmethyl ferulate comprises reacting 4-hydroxycinnamoyliodomethane with sodium or potassium salt of ferulic acid in step A.

6. The process according to claim 2 wherein synthesis of 4-Hydroxycinnamoylmethyl 4-hydroxycinnamate comprises reacting 4-hydroxycinnamoyliodomethane with sodium or potassium salt of 4-hydroxycinnamic acid in step A.

7. The process according to claims 1 and 2 wherein the solvent used in step A is one selected from group comprising dichloromethane, chloroform, ethyl acetate and tetrahydrofuran.

8. The process according to claims 1 and 2 wherein the phase transfer catalyst used in step B is one selected from group consisting of tetrabutylammonium bromide, tetrabutylammonium hydrogensulfate, benzyltributyl ammonium chloride, benzyltriethylammonium chloride and benzyltrimethyl ammonium chloride.

* * * * *